United States Patent [19]

Miya et al.

[11] Patent Number: 4,874,880

[45] Date of Patent: Oct. 17, 1989

[54] BIS(DI-, TRI- OR TETRA-SUBSTITUTED-CYCLOPENTADIENYL)-ZIRCONIUM DIHALIDES

[75] Inventors: Shinya Miya, Ichiharashi; Masato Harada, Kisarazushi; Takaya Mise, Kawagoeshi; Hiroshi Yamazaki, Tokorozawashi, all of Japan

[73] Assignees: Chisso Corporation; The Institute of Physical & Chemical Research, both of Japan

[21] Appl. No.: 158,924

[22] Filed: Feb. 22, 1988

[30] Foreign Application Priority Data

Mar. 10, 1987 [JP] Japan .................................. 62-54367
Mar. 10, 1987 [JP] Japan .................................. 62-54368
Mar. 10, 1987 [JP] Japan .................................. 62-54369
Mar. 23, 1987 [JP] Japan .................................. 62-68630
Mar. 25, 1987 [JP] Japan .................................. 62-71157

[51] Int. Cl.$^4$ ............................................. C07F 7/00
[52] U.S. Cl. ........................................ 556/53; 502/117
[58] Field of Search ................................... 556/53

[56] References Cited

U.S. PATENT DOCUMENTS

| | | | |
|---|---|---|---|
| 2,827,446 | 3/1958 | Breslow | 556/53 X |
| 2,864,843 | 12/1958 | DeWitt | 556/53 X |
| 2,868,751 | 1/1959 | Johnson | 556/53 X |
| 2,911,424 | 11/1959 | Kaufman | 556/53 X |
| 2,952,670 | 9/1960 | Fischer | 556/53 X |
| 2,983,740 | 5/1961 | Thomas | 556/53 |
| 2,983,741 | 5/1961 | Brantley | 556/53 |
| 3,347,887 | 10/1967 | Gissings | 556/53 X |
| 4,147,709 | 4/1979 | Lynch | 556/53 |

FOREIGN PATENT DOCUMENTS

3127133 1/1983 Fed. Rep. of Germany .

OTHER PUBLICATIONS

Geetha, S., et al., (Univ. Kerala, Thuardrum, India), "*Indian Journal of Chemistry*", 1969 7(5), 518.

Kaminsky, W., "Bis(Cyclopatadieayl) Zirkon-Verbirgdungen and Aluminoxarals Ziegler-Katalysaturen Für Die Polymerisation and Copolymerization Ion Olefines", Makrom. Chem. Rapid Commun., 4, 417 (1983).

*Primary Examiner*—H. M. S. Sneed
*Assistant Examiner*—George R. Fourson
*Attorney, Agent, or Firm*—Fred Philpitt

[57] ABSTRACT

Bis(di-, tri- or tetra-substituted-cyclopentadienyl)zirconium dihalides represented by the following general formula [I] are provided,

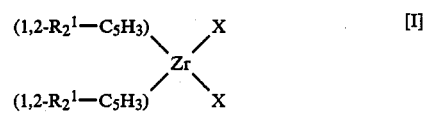

(wherein $R^1$ denotes a substituent group on the cyclopentadienyl ring which is an alkyl radical of 1 to 5 carbon atoms; $R_2^1$—$C_5H_3$ stands for a di-substituted cyclopentadienyl radical; and X is a halogen atom).

This compound, when combined with an aluminoxane repesented by the following general formula [VII], gives a high-activity catalyst for the synthesis of polyolefins,

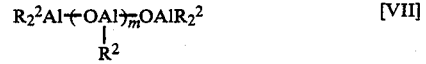

(wherein m is an integer of 4 to 20; and $R^2$ denotes a hydrocarbyl radical).

3 Claims, 16 Drawing Sheets

BIS(DI-, TRI- OR TETRA-SUBSTITUTED-CYCLOPENTADIENYL)-ZIRCONIUM DIHALIDES

BACKGROUND OF THE INVENTION

1. Field of the Invention

This invention relates to bis(di-, tri- or tetra-substituted-cyclopentadienyl)zirconium dihalides, to a high-activity catalyst for the synthesis of polyolefins comprising the same, and to a process for producing polyolefins using said catalyst.

2. Description of the Prior Art

Since a catalyst comprising a bis(di-substituted-cyclopentadienyl)zirconium dichloride and methylaluminoxane was found to have high activity for polymerizing olefins [Japanese Patent Kokai No. 19309 (1983), and Makromol. Chem. Rapid Commun, 4, 417 (1983)], various types of zirconium compounds have been investigated as a component of olefinpolymerization catalysts.

As examples of cyclopentadienyl zirconium compounds having sustituent groups on the cyclopentadienyl ring so far synthesized, may be mentioned bis(methylcyclopentadienyl)zirconium dichloride [J. Chem. Soc. Dalton Trans., 805 (1981)], bis((pentamethylcyclopentadienyl)zirconium dichloride [J. Amer. Chem. Soc., 100, 3078 (1978)] and (pentamethylcyclopentadientyl)-(cyclopentadienyl)zirconium dichloride [J. Amer. Chem. Soc., 106, 6355 (1984)]. However, no zirconium compound having, as ligand, two di-, tri- or tetra-substituted-cyclopentadienyl radicals has yet been synthesized.

Use of compounds represented by the general formula of $(C_5R_m')_pR_s''(C_5R_m')MeQ_{3-p}$ or $R_s''(C_5R_m')_2MeQ$ as catalysts is described in Japanese Patent Kokai No. 35006 through No. 35008 (1985) and No. 296008 (1986), but no description can be found at all on the synthesis and properties of these compounds.

Japanese Patent Kokai No. 236804 (1986) describes a process for producing polyethylene wax with unsaturated bonds at terminals, but no description is made on the details of said unsaturated bonds.

These conventional Kaminsky catalysts have the problems that the yield and molecular weight of resultant polyolefins are not sufficiently high, and that there is no controlling the structure of said unsaturated bonds at terminals.

SUMMARY OF THE INVENTION

We succeeded in preparing the aforementioned zirconium compounds having, as ligand, two di-, tri- or tetra-substituted-cyclopentadienyl radicals (novel compounds useful as a component of polyolefin-producing catalysts) through the route shown later—equations (1) and (2)—, and also proved the intended effectiveness of these compounds.

Thus, we found that catalysts comprising a novel transition metal compound as mentioned above and a specific aluminoxane catalyze polymerization of olefins to produce polyolefins with controlled terminal groups (vinylidene type), and accomplished this invention based on these findings.

As may be apparent from the foregoing, the object of this invention is to provide the novel and useful zirconium compounds mentioned above and uses thereof.

The zirconium compounds of this invention are represented by the following general formula [X], [Y] or [Z],

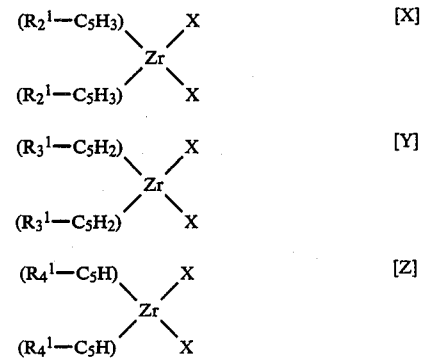

wherein $R^1$ denotes a substituent group on the cyclopentadienyl ring which is an alkyl radical of 1 to 5 carbon atoms; $R_2^1\text{-}C_5H_3$, $R_3^1\text{-}C_5H_2$ and $R_4^1\text{-}C_5H$ stand for a di-, tri- and tetra-substituted cyclopentadienyl radicals, respectively; and X is a halogen atom.

The zirconium compounds of this invention, [X], [Y] and [Z], contain as ligand di-, tri- and tetra-substituted cyclopentadienyl radicals, respectively, and include the following structures ([I] and [II]; [III] and [IV]; and [V] respectively),

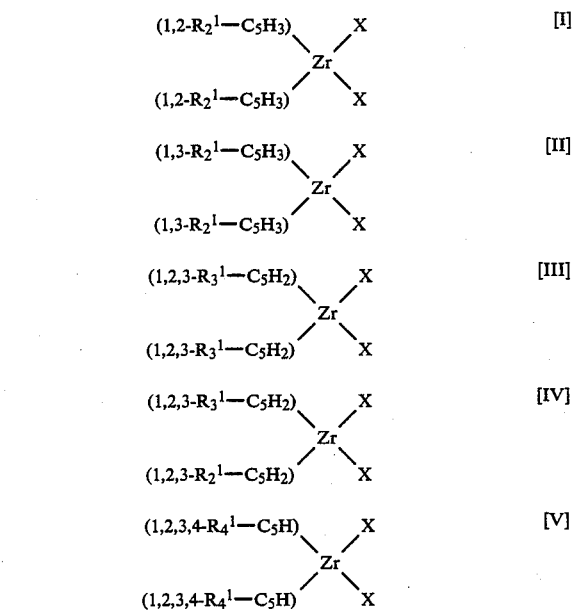

wherein $R^1$, $R_2^1\text{-}C_5H_3$, $R_3^1\text{-}C_5H_2$, $R_4^1\text{-}C_5H$ and X are as defined above; and the numerals ahead of each $R^1$ determine its position on the cyclopentadienyl ring.

The catalyst of this invention and the process for producing polyolefins using the same are as specified below.

(1) Catalyst for the synthesis of polyolefins which contains, as effective components, (A) a transition metal compound represented by the following general formula (VI),

$(R_n^1\text{-}C_5H_{5-n})_2MX_2$  [VI]

(wherein $R_n^1$-$C_5H_{5-n}$ denotes a substituted-cyclopentadienyl radical; n is an integer of 2 to 4; $R^1$ stands for an alkyl radical of 1 to 5 carbon atoms; M expresses titanium, zirconium, vanadium or hafnium; and X is a halogen atom), and (B) an aluminoxane represented by the following general formula [VII] or [VIII],

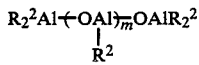  [VII]

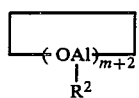  [VIII]

(wherein m is an integer of 4 to 20; and $R^2$ denotes a hydrocarbyl radical).

(2) The catalyst as described in (1) above wherein M in said transition metal compound [VI] is zirconium and X is chlorine.

(3) The catalyst as described in (1) above wherein $R_n^1$-$C_5H_{5-n}^1$ a is 1,2-, 1,3-, 1,2,3-, 1,2,4- or 1,2,3,4-substituted-cyclopentadienyl radical.

(4) Process for producing polyolefins by using a catalyst described in (1), (2) or (3) above.

DESCRIPTION OF THE PREFERRED EMBODIMENT

Figure 1:
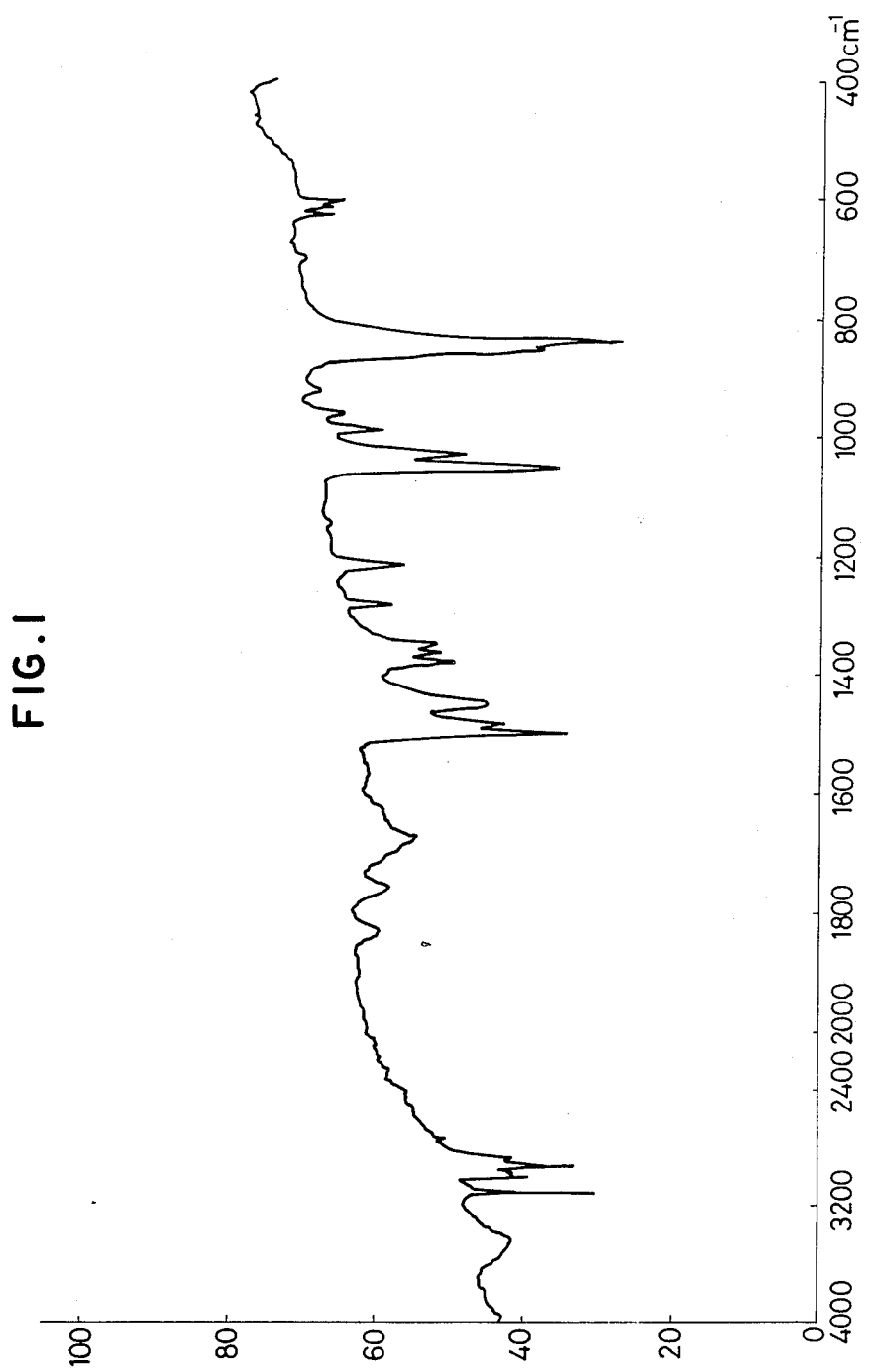
FIGS. 1, 3, 5, 7 and 9 show IR spectra of the compounds of this invention.

In the zirconium compounds of this invention represented by the general formula [X], [Y] or [Z], $R^1$ is a hydrocarbyl radical such as methyl, ethyl, propyl, isopropyl, butyl, sec-butyl, tert-butyl and pentyl, preferably methyl or ethyl; and X is a halogen atom such as fluorine, chlorine, bromine and iodine, preferably chlorine.

Compounds [X] may be prepared through the synthetic route shown below (the same is true of compounds [Y] and [Z]), $R_2^1$-$C_5H_4$ + n-BuLi → Li($R_2^1$-$C_5H_3$) + n-Butane  (1)

2Li($R_2^1$-$C_5H_3$) + ZrX$_4$ → ($R_2^1$-$C_5H_3$)$_2$ZrX$_2$ + 2LiX  (2)

wherein $R^1$, $R_2^1$-$C_5H_3$ and X are as defined above.

Di-substituted cyclopentadienes are of the following two types:

(1,2-$R_2^1$—$C_5H_4$)

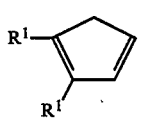

(1,3-$R_2^1$—$C_5H_4$)

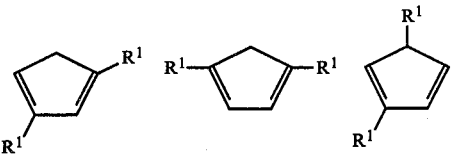

All the isomers shown above are included in this invention.

Tri-substituted cyclopentadienes are of the following two types:

(1,2,3-$R_3^1$—$C_5H_3$)

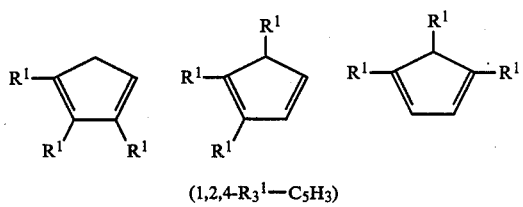

(1,2,4-$R_3^1$—$C_5H_3$)

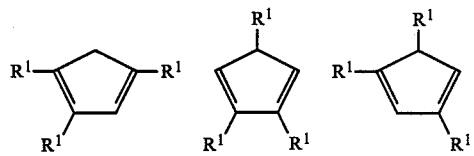

All the isomers shown above are included in this invention.

Tetra-substituted cyclopentadienes are of 1,2,3,4-$R_4^1$-$C_5H_2$ type:

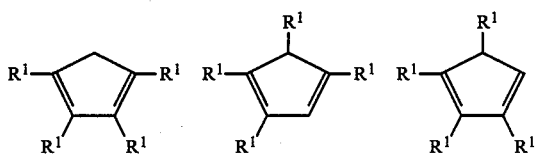

All the isomers shown above are included in this invention.

Substituted cyclopentadienes of this type can be prepared by known methods described in Bull. Soc. Chim. Fr., 2981 (1970), J. Chem. Soc., 1127 (1952), Tetrahedron, 19, 1939 (1963), ibid., 21, 2313 (1965) and J. Org. Chem., 36, 3979 (1971).

These substituted cyclopentadienes may be converted to the corresponding Li compounds by reaction with an alkyl lithium to be subjected to the succeeding reaction. Alternatively, substituted cyclopentadienyl potassium or substituted cyclopentadienyl sodium may also be used similarly.

Reaction of ZrX$_4$ with Li($R_2^1$-$C_5H_3$), Li($R_3^1$-$C_5H_2$) or Li($R_4^1$-$C_5H$) may be carried out in an ether solvent, preferably tetrahydrofuran (THF) or 1,2-dimethoxyethane, at a temperature in the range from −20° to 100° C. (preferably from 0° to 30° C.). The preferred mole ratio of Li($R_2^1$-$C_5H_3$), Li($R_3^1$-$C_5H_2$) or Li($R_4^1$-$C_5H$) to ZrX$_4$ is in the range from 1.9 to 3.0, most preferably from 2.0 to 2.4. The reaction is complete in three days at room temperature, and can be completed in shorter periods at elevated temperatures. The reaction products, represented by the formula [X], [Y] or [Z], may be purified by recrystallization or sublimation.

As illustrative examples of the compounds represented by formula [VI], there may be mentioned titanium compounds, such as bis(1,2-dimethylcyclopentadienyl)titanium dichloride, bis(1,2-diethylcyclopentadienyl)titanium dichloride, bis(1,2-dimethylcyclopentadienyl)titanium dibromide, bis(1,3-dimethylcyclopentadienyl)titanium dichloride, bis(1,2,3-trimethylcyclopentadienyl)titanium dichloride, bis(1,2,4-trimethylcyclopentadienyl)titanium dichloride and bis(1,2,3,4-tetramethylcyclopentadienyl)titanium dichloride; zirconium compounds, such as bis(1,2-dimethylcyclopentadienyl)zirconium dichloride, bis(1,2-diethylcyclopentadienyl)zirconium dichloride, bis(1,3-dimethylcyclopentadienyl)zirconium dichloride, bis(1,3-diethylcyclopentadienyl)zirconium dichloride, bis(1,3-dimethylcyclopentadienyl)zirconium dibromide, bis(1,2,3-trimethylcyclopentadienyl)zirconium dichloride, bis(1,2,3-trimethylcyclopentadienyl)zirconium dibromide, bis(1,2,4-trimethylcyclopentadienyl)zirconium dichloride, bis(1,2,4-trimethylcyclopentadienyl)zirconium dibromide, bis(1,2,4-trimethylcyclopentadienyl)zirconium diiodide, bis(1,2,4-trimethylcyclopentadienyl)zirconium difluoride, bis(1,2,3,4-tetramethylcyclopentadienyl)zirconium dichloride and bis(1,2,3,4-tetramethylcyclopentadienyl)zirconium dibromide; hafnium compounds, such as bis(1,2-dimethylcyclopentadienyl)hafnium dichloride, bis(1,3-dimethylcyclopentadienyl)hafnium dichloride, bis(1,2,3-trimethylcyclopentadienyl)hafnium dichloride, bis(1,2,4-trimethylcyclopentadienyl)hafnium dichloride and bis(1,2,3,4-tetramethylcyclopentadienyl)hafnium dichloride; and vanadium compounds, such as bis(1,2-dimethylcyclopentadienyl)vanadium dichloride, bis(1,3-dimethylcyclopentadienyl)vanadium dichloride, bis(1,2,3-trimethylcyclopentadienyl)vanadium dichloride, bis(1,2,4-trimethylcyclopentadienyl)vanadium dichloride and bis(1,2,3,4-tetramethylcyclopentadienyl)vanadium dichloride.

Of these compounds, bis(1,3-dimethylcyclopentadienyl)zirconium dichloride, bis(1,2,4-trimethylcyclopentadienyl)zirconium dichloride and bis(1,2,3,4-tetramethylcyclopentadienyl)zirconium dichloride are the most preferred.

Aluminoxane (B), which is the other component of the catalyst of this invention, is an organo-aluminum compound represented by the general formula [VII] or [VIII]. $R^2$ is a hydrocarbyl radical, such as methyl, ethyl, propyl and butyl (preferably methyl or ethyl), and m is an integer of 4 to 20, preferably 6 to 20, most preferably 10 to 20. These compounds may be prepared by known methods, for example, by adding a trialkyl aluminum to a suspension of a compound with absorbed water or a salt with water of crystallization (e.g., hydrated cupric sulfate and hydrated aluminum sulfate) in a hydrocarbon medium.

The olefins to be used for polymerization by the catalyst of this invention are α-olefins, such as ethylene, propylene, 1-butene, 4-methyl-1-pentene, 1-hexene, 1-octene, 1-decene, 1-dodecene, 1-tetradecene, 1-hexadecene, 1-octadecene and 1-eicosene. These may be polymerized either alone or in combination. In addition, the catalyst of this invention may be used for copolymerization of such an α-olefin with a diene, such as butadiene, 1,4-hexadiene, 1,4-pentadiene, 1,7-octadiene, 1,8-nonadiene and 1,9-decadiene; or with a cyclic olefin, such as cyclopropane, cyclobutene, cyclohexene, norbornene and cyclopentadiene.

Polymerization may be effected by any of the suspension, solution and gas-phase polymerization methods. As the solvent in solution polymerization, may be used an alifatic hydrocarbon, such as butane, pentane, hexane, octane, decane, dodecane, hexadecane and octadecane; an alicyclic hydrocarbon, such as cyclopentane, methylcyclopentane, cyclohexane and cyclooctane; an aromatic hydrocarbon, such as benzene, toluene and xylene; or a petroleum fraction, such as gasoline, kerosene and gas oil. Of these, aromatic hydrocarbons are the most preferred. Polymerization is carried out at a temperature in the range from −50° to 230° C. (preferably from −20° to 200° C.) under an olefin pressure in the range from normal pressure to 50 $Kg/cm^2G$. Molecular weight of polyolefins can be modified by known techniques, for example, by selection of proper polymerization temperature or by introduction of hydrogen gas into the reaction system.

In carrying out olefin polymerization, the two components of catalyst (A) and (B) (a transition metal compound and an aluminoxane) may be added to the reaction system after being intimately mixed together, or may be separately introduced to the reaction system. In both cases, there is no specific limitation upon the mole ratio and concentration of the two components in the system. But it is preferable that the concentration of component (A) be in the range from $10^{-4}$ to $10^{-9}$ mol/l and the Al/transition-metal-atom mole ratio be 100 or higher (most preferably 1000 or higher).

The structure of terminal unsaturated bond in polyolefins produced by the use of catalyst of this invention can be identified by IR analysis. For example, vinylidene group can be detected by the presence of absorption peaks at 3095 to 3077 $cm^{-1}$, 1790 to 1785 $cm^{-1}$, 1661 to 1639 $cm^{-1}$ and 892 to 883 $cm^{-1}$.

Use of a catalyst of this invention, which comprises an aluminoxane and a novel transition metal compound having two di-, tri- or tetra-substituted cyclopentadienyl radicals, gives polyolefins with controlled structure of terminal groups (vinylidene type).

As will be apparent from the following Examples and Comparative Examples, the catalyst of this invention is higher in activity and gives polyolefins with higher molecular weight, compared with conventional catalyst systems. In addition, molecular weight distribution of the resultant polyolefins can be easily regulated if several kinds of the novel transition metal compounds are used in the catalyst.

The following Examples will further illustrate the invention.

EXAMPLE 1

[Bis(1,2-dimethylcyclopentadienyl)zirconium dichloride]

The reaction was carried out in an inert gas atmosphere throughout its entire course. The solvent used for reaction had been previously dehydrated. To a solution of 2.0 g (21 millimoles) 1,2-dimethylcyclopentadiene in 150 ml tetrahydrofuran placed in a glass reaction vessel (500 ml), was added dropwise 16 ml of a 15% solution of n-butyl lithium in hexane at 0° C., the mixture was stirred at room temperature for one hour, the resulting solution of 1,2-dimethylcyclopentadienyl lithium was cooled to 0° C., and 2.4 g (10 millimoles) zirconium tetrachloride was added in five portions.

The temperature of reaction mixture was slowly raised to room temperature, stirring was continued for 12 hours, the solvent was distilled off under reduced pressure from the yellow solution containing white precipitate (LiCl), and the crude product thus left was purified by sublimation (120°–140° C./1 mmHg), giving pure product as white crystals (yield: 0.25 g, 7%). Its properties are shown below, in which IR spectrum and $^1$H-NMR spectrum were measured by the KBr and CDCl$_3$ (100 MHz) methods, respectively.

Figure 2:
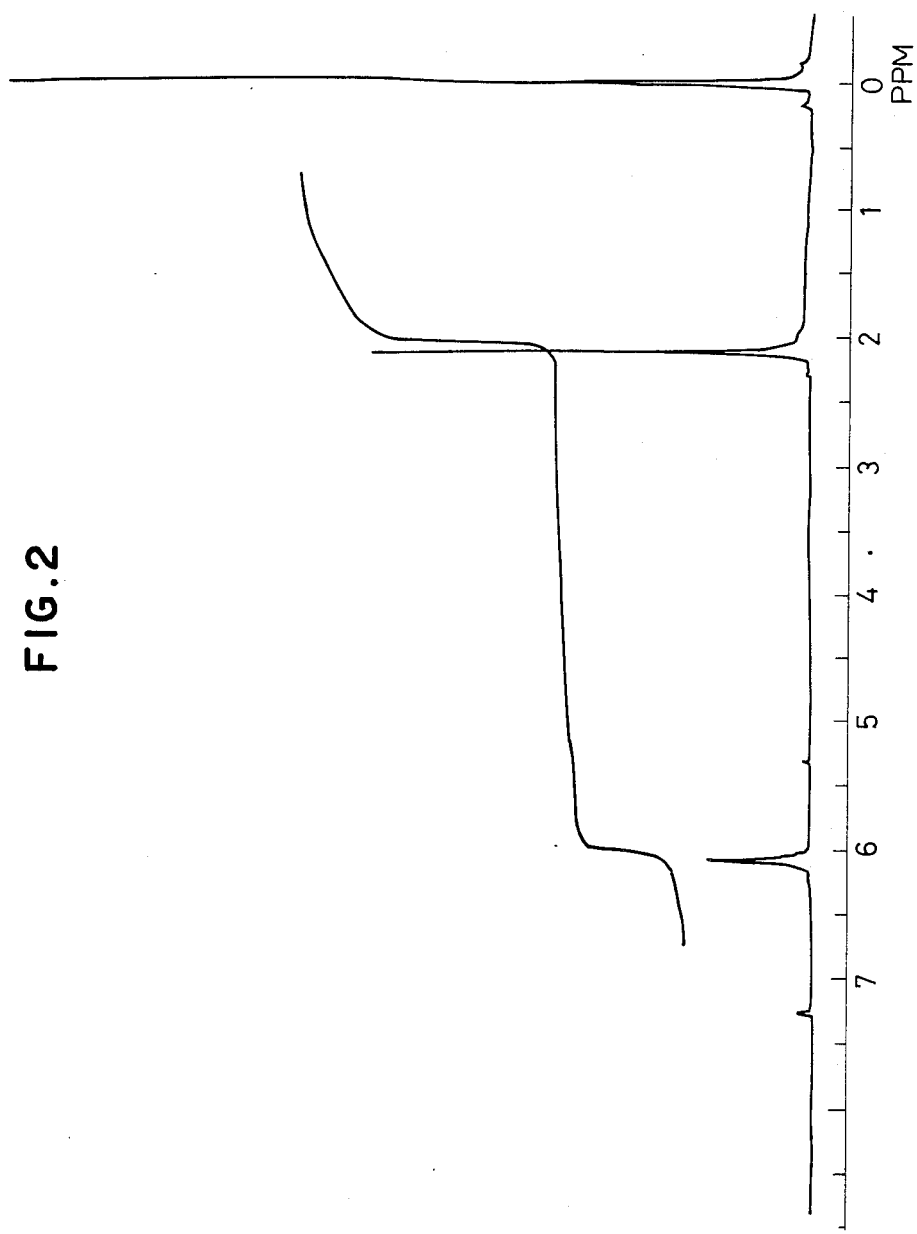
FIGS. 2, 4, 6, 8 and 10 show NMR spectra of the compounds of this invention.

Melting point: 252°–254° C.
Elemental analysis (C$_{14}$H$_{18}$Cl$_2$Zr): Calcd. (%) C: 48.26, H: 5.21; Found (%) C: 48.10, H: 5.06.
IR spectrum: As shown in FIG. 1
NMR spectrum: As shown in FIG. 2

EXAMPLE 2

[Bis(1,3-dimethylcyclopentadienyl)zirconium dichloride]

The reaction was carried out in an inert gas atmosphere throughout its entire course. The solvent used for reaction had been previously dehydrated. To a solution of 3.4 g (36 millimoles) 1,3-dimethylcyclopentadiene in 150 ml tetrahydrofuran placed in a glass reaction vessel (500 ml), was added dropwise 24 ml of a 15% solution of n-butyl lithium in hexane at 0° C., the mixture was stirred at room temperature for one hour, the resulting solution of 1,3-dimethylcyclopentadienyl lithium was cooled to 0° C., and 3.5 g (15 millimoles) zirconium tetrachloride was added in five portions.

The temperature of reaction mixture was slowly raised to room temperature, stirring was continued for 48 hours, the solvent was distilled off under reduced pressure from the yellow solution containing white precipitate (LiCl), and the residue was extracted with 300 ml dichloromethane. The yellow extract was concentrated, pentane was added, and the resulting mixture was cooled to −30° C., giving 1.7 g of white crystals. The crude product thus obtained was purified by sublimation (130°–140° C./1 mmHg), affording pure product (yield: 1.1 g, 22%). Its properties are shown below, in which IR spectrum and $^1$H-NMR spectrum were measured by the KBr and CDCl$_3$ (100 MHz) methods, respectively.

Figure 3:
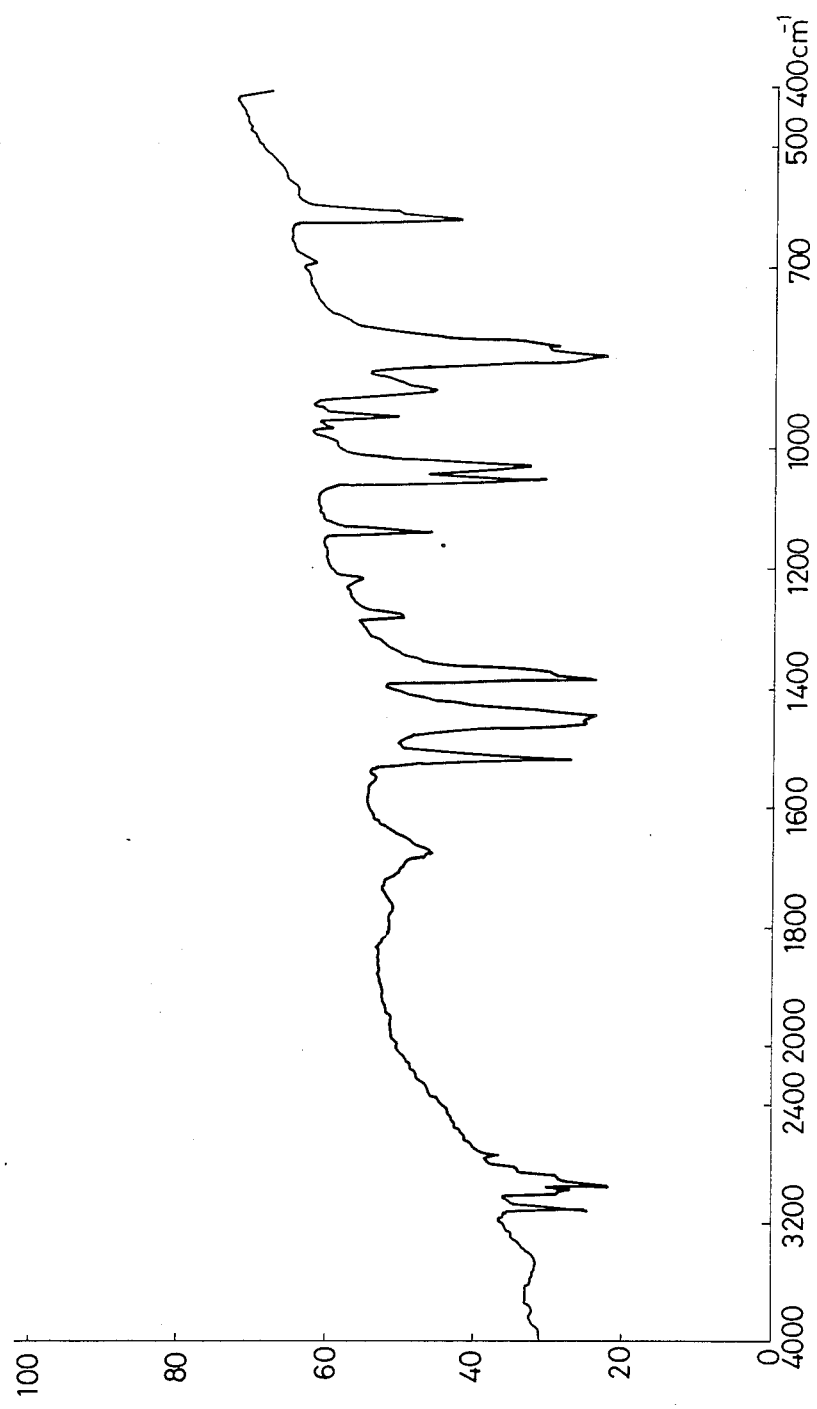
Figure 4:
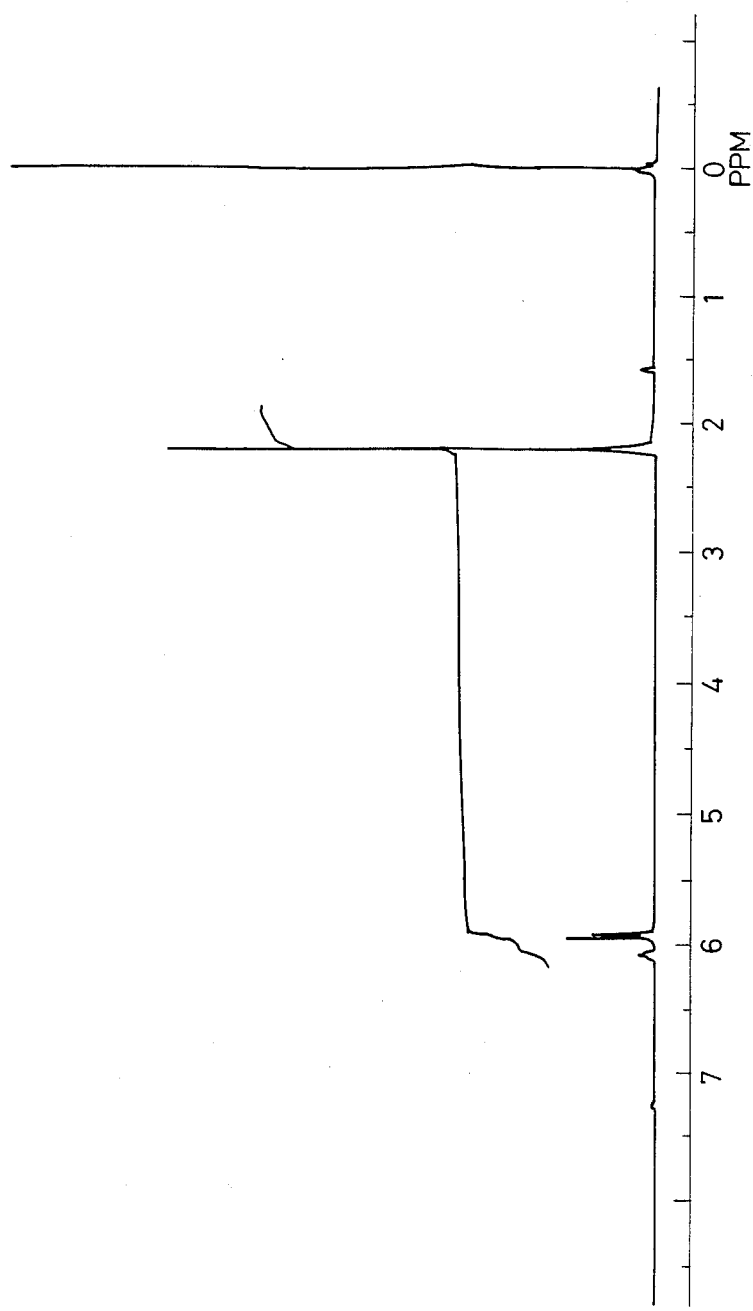

Melting point: 175°–176° C.
Elemental analysis (C$_{14}$H$_{18}$Cl$_2$Zr): Calcd. (%) C: 48.26, H: 5.21; Found (%) C: 48.45, H: 5.09.
IR spectrum: As shown in FIG. 3
NMR spectrum: As shown in FIG. 4

EXAMPLE 3

[Bis(1,2,3-trimethylcyclopentadienyl)zirconium dichloride]

The reaction was carried out in an inert gas atmosphere throughout its entire course. The solvent used for reaction had been previously dehydrated. To a solution of 3.5 g (32 millimoles) 1,2,3-trimethylcyclopentadiene in 150 ml tetrahydrofuran placed in a glass reaction vessel (500 ml), was added dropwise 25 ml of a 15% solution of n-butyl lithium in hexane, the mixture was stirred at room temperature for one hour, the resulting white suspension of 1,2,3-trimethylcyclopentadienyl lithium was cooled to 0° C., and 3.7 g (16 millimoles) zirconium tetrachloride was added in five portions.

The temperature of reaction mixture was slowly raised to room temperature, stirring was continued for three hours, the solvent was distilled off under reduced pressure from the yellow solution containing white precipitate (LiCl), and the crude product thus left was purified by sublimation (130°–140° C./1 mmHg), giving pure product as white crystals (yield: 0.68 g, 11%). Its properties are shown below, in which IR spectrum and $^1$H-NMR spectrum were measured by the KBr and CDCl$_3$ (400 MHz) methods, respectively.

Figure 5:
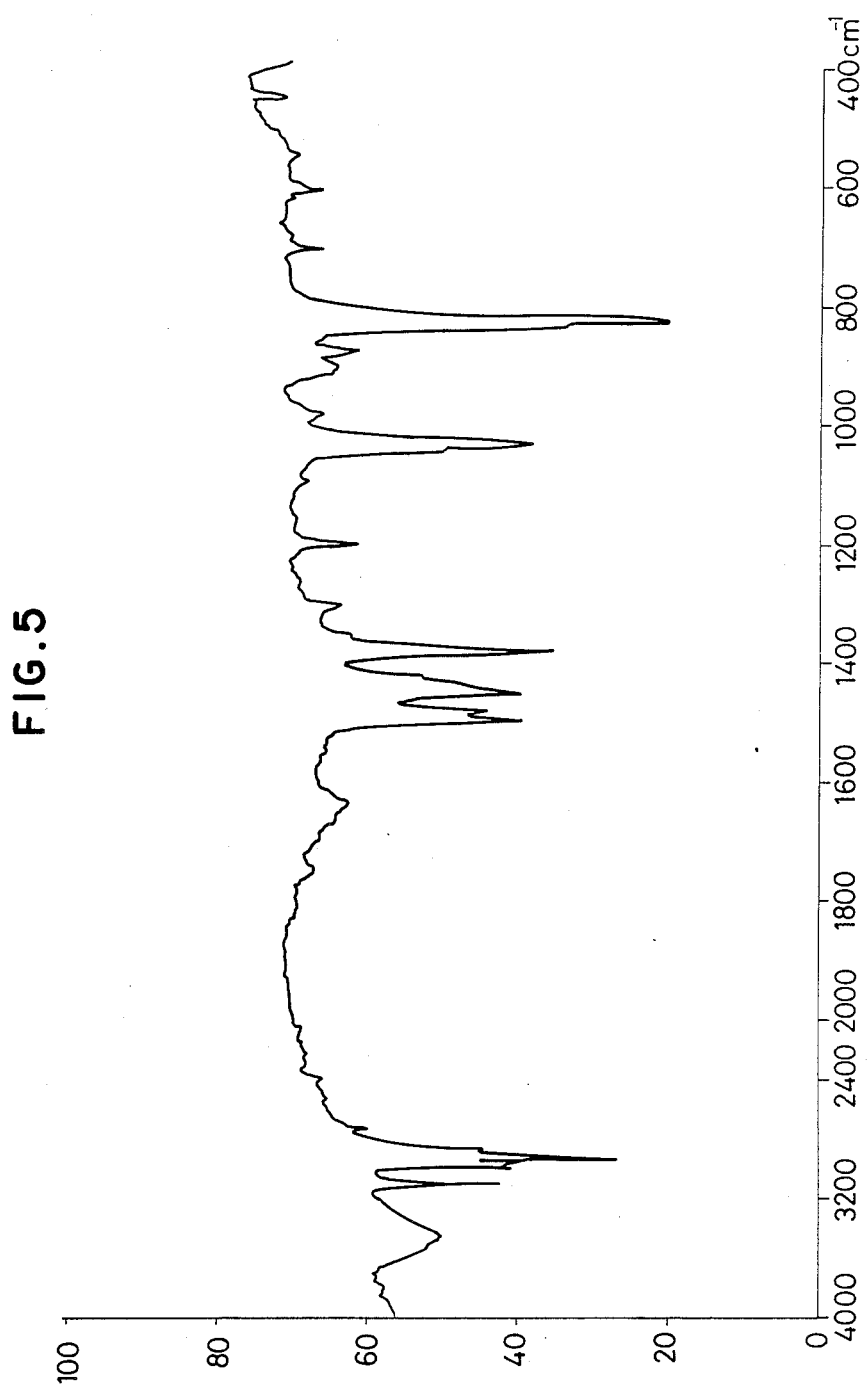
Figure 6:
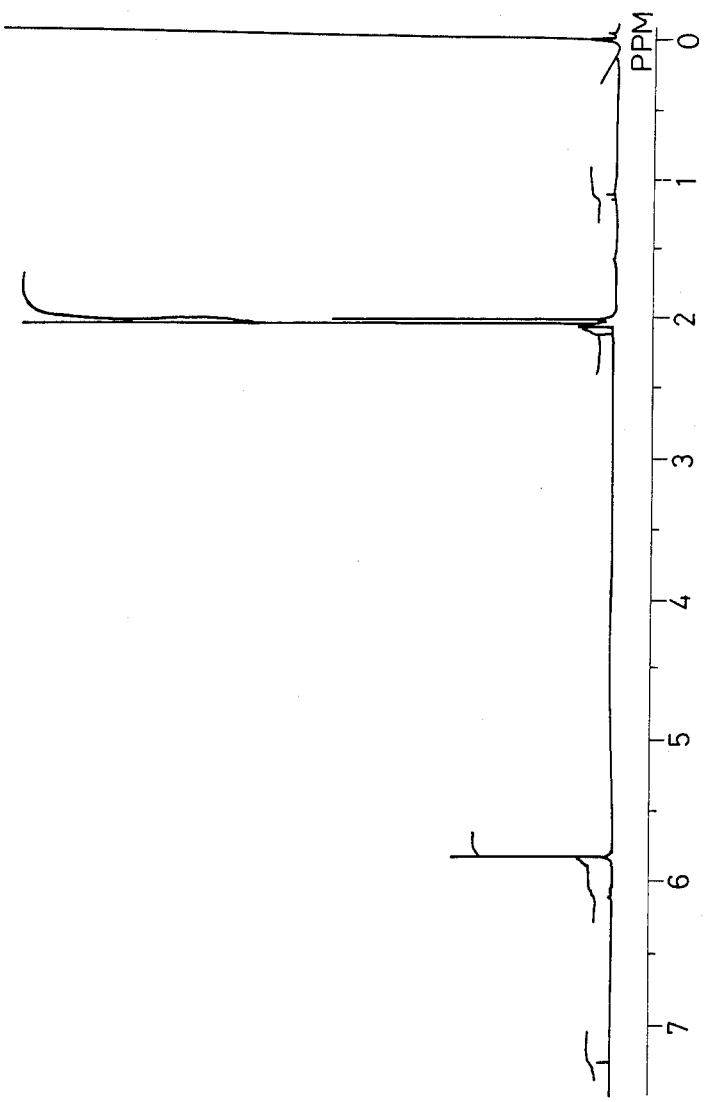

Melting point: 252°–253° C.
Elemental analysis (C$_{16}$H$_{22}$Cl$_2$Zr): Calcd. (%) C: 51.05, H: 5.89; Found (%) C: 50.96, H: 5.83.
IR spectrum: As shown in FIG. 5
NMR spectrum: As shown in FIG. 6

EXAMPLE 4

[Bis(1,2,4-trimethylcyclopentadienyl)zirconium dichloride]

The reaction was carried out in an inert gas atmosphere throughout its entire course. The solvent used for reaction had been previously dehydrated. To a solution of 5.5 g (51 millimoles) 1,2,4-trimethylcyclopentadiene in 150 ml tetrahydrofuran placed in a glass reaction vessel (500 ml), was added dropwise 36 ml of a 15% solution of n-butyl lithium in hexane, the mixture was stirred at room temperature for one hour, the resulting white suspension of 1,2,4-trimethylcyclopentadienyl lithium was cooled to 0° C., and 5.9 g (25 millimoles) zirconium tetrachloride was added in five portions.

The temperature of reaction mixture was slowly raised to room temperature, stirring was continued for 48 hours, the solvent was distilled off under reduced pressure from the yellow solution containing white precipitate (LiCl), and the residue was extracted with 300 ml dichloromethane. The yellow extract was cocnetrated, pentane was added, and the resulting mixture was cooled to −30° C., giving 4.0 g of white crystals. The crude product thus obtained was purified by sublimation (130°–140° C./1 mmHg), affording pure product (yield: 3.5 g, 36%). Its properties are shown below, in which IR spectrum and $^1$H—NMR spectrum were measured by the KBr and CDCl$_3$ (100 MHz) methods, respectively.

Figure 7:
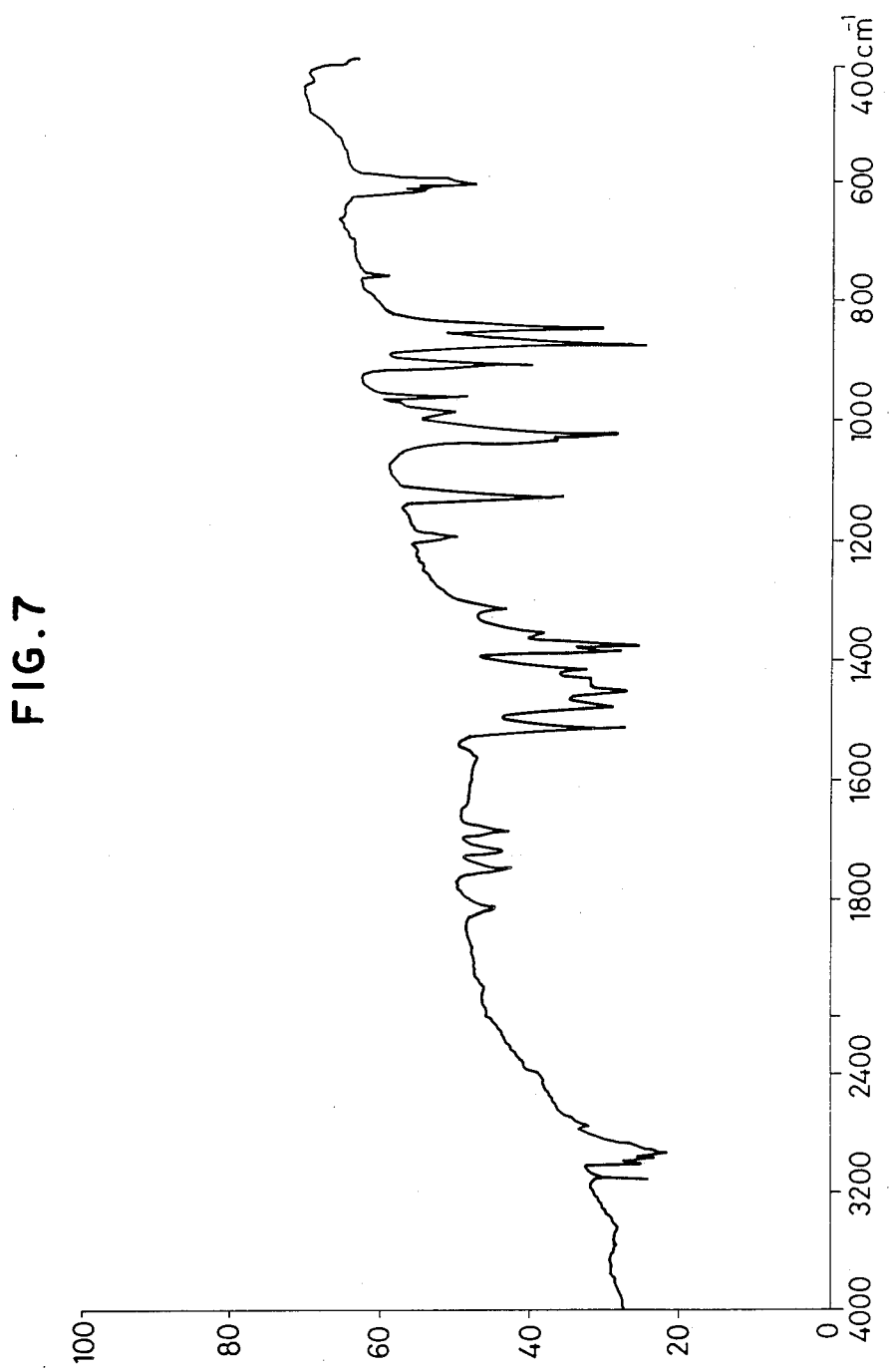
Figure 8:
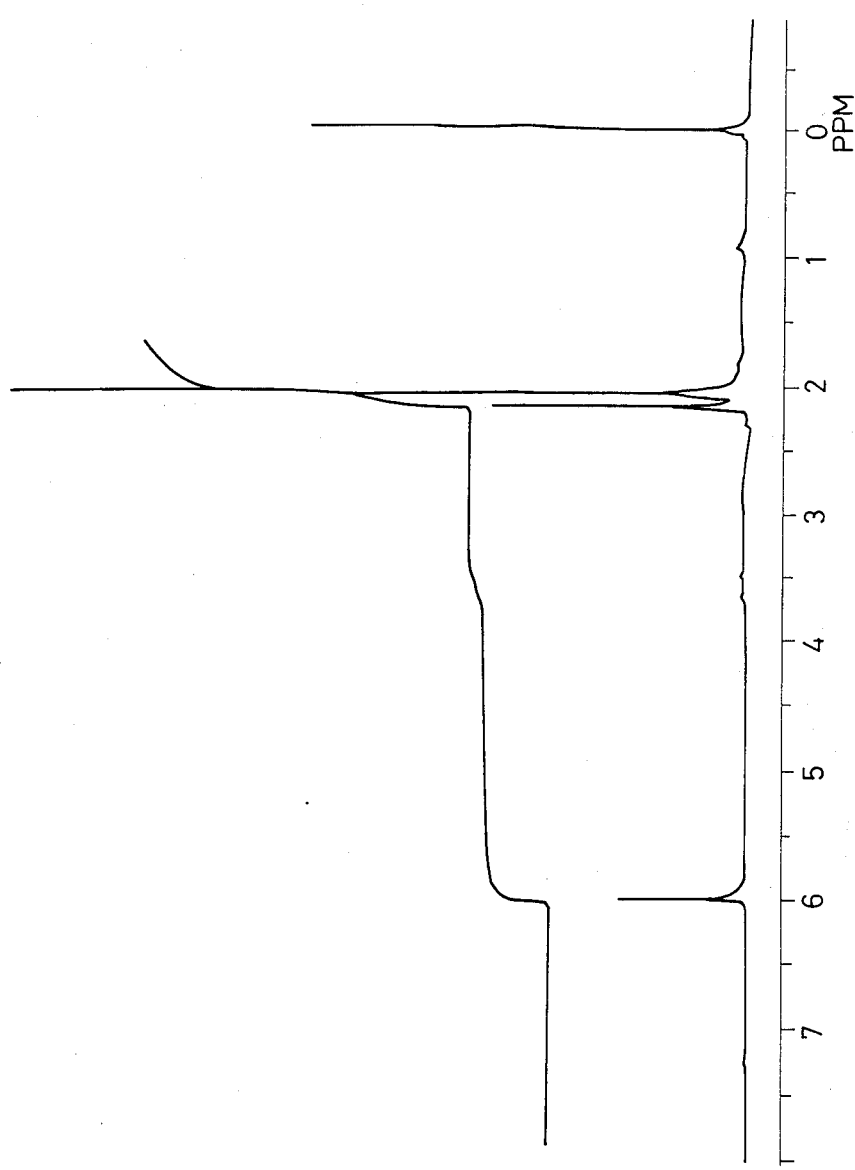

Melting point: 172°–173° C.
Elemental analysis (C$_{16}$H$_{22}$Cl$_2$Zr): Calcd. (%) C: 51.05, H: 5.89; Found (%) C: 51.02, H: 5.75.
IR spectrum: As shown in FIG. 7
NMR spectrum: As shown in FIG. 8

EXAMPLE 5

[Bis(1,2,3,4-tetramethylcyclopentadienyl)zirconium dichloride]

The reaction was carried out in an inert gas atmosphere throughout its entire course. The solvent used for reaction had been previously dehydrated. To a solution of 2.5 g (20 millimoles) 1,2,3,4-tetramethylcyclopentadiene in 150 ml tetrahydrofuran placed in a glass reaction vessel (500 ml), was added dropwise 15 ml of a 15% solution of n-butyl lithium in hexane, the mixture was stirred at room temperature for one hour, the resulting white suspension of 1,2,3,4-tetramethylcyclopentadienyl lithium was cooled to 0° C., and 2.3 g (10 millimoles) zirconium tetrachloride was added in five portions.

The reaction mixture was heated under reflux for 72 hours, the solvent was distilled off under reduced pressure from the yellow solution containing white precipitate (LiCl), and the residue was extracted with 300 ml dichloromethane. The yellow extract was cocentrated, pentane was added, and the resulting mixture was cooled to −30° C., giving 0.16 g of white crystals. The crude product thus obtained was purified by sublimation (130°-140° C./1 mmHg), affording pure product (yield: 0.13 g, 3%). Its properties are shown below, in which IR spectrum and $^1$H—NMR spectrum were measured by the KBr and CDCl$_3$ (400 MHz) methods, respectively.

Melting point: 270°-271° C.

Elemental analysis (C$_{18}$H$_{26}$Cl$_2$Zr): Calcd. (%) C: 53.44, H: 6.48; Found (%) C: 53.43, H: 6.49.

Figure 9:
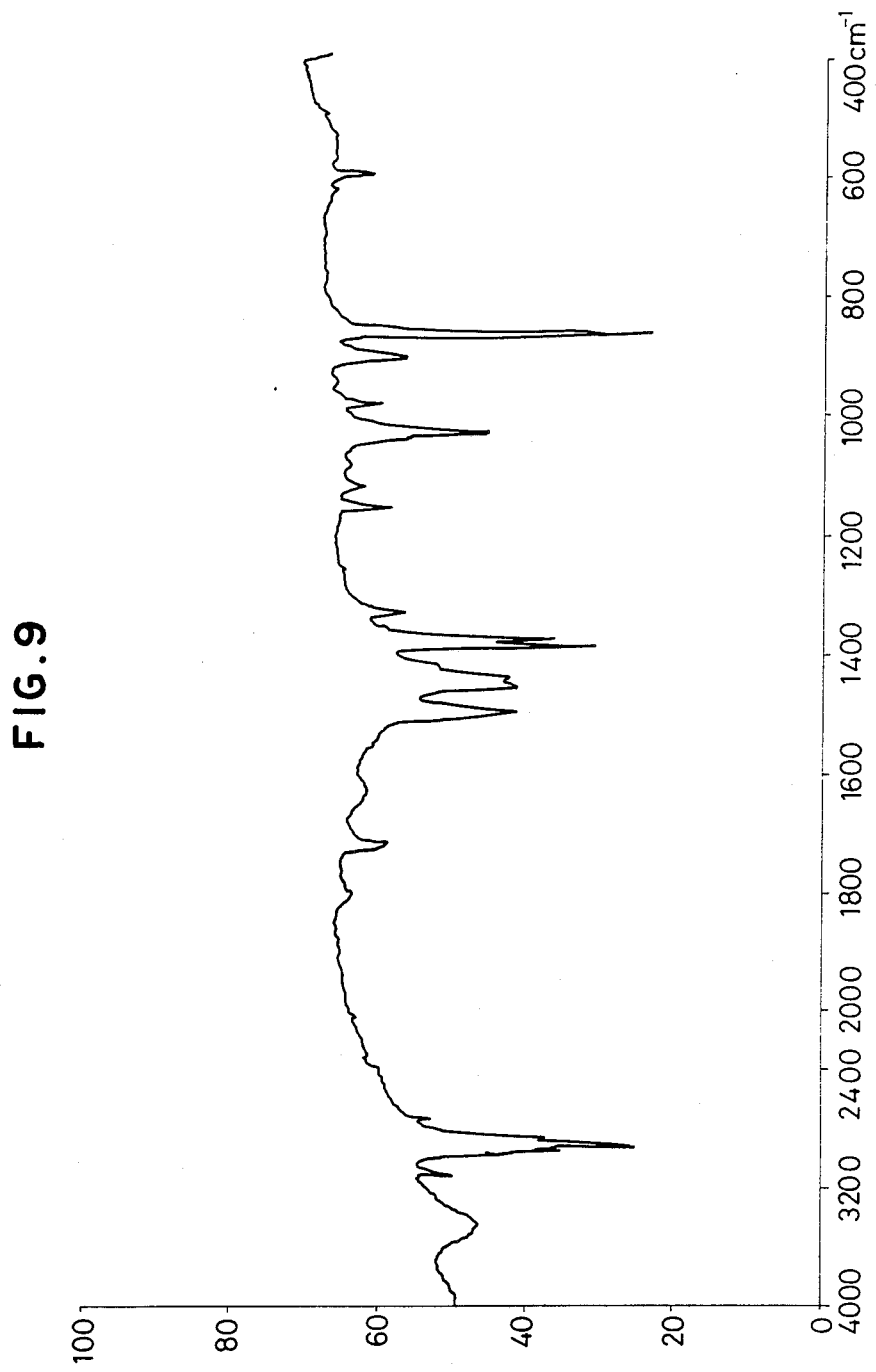

IR spectrum: As shown in FIG. 9

Figure 10:
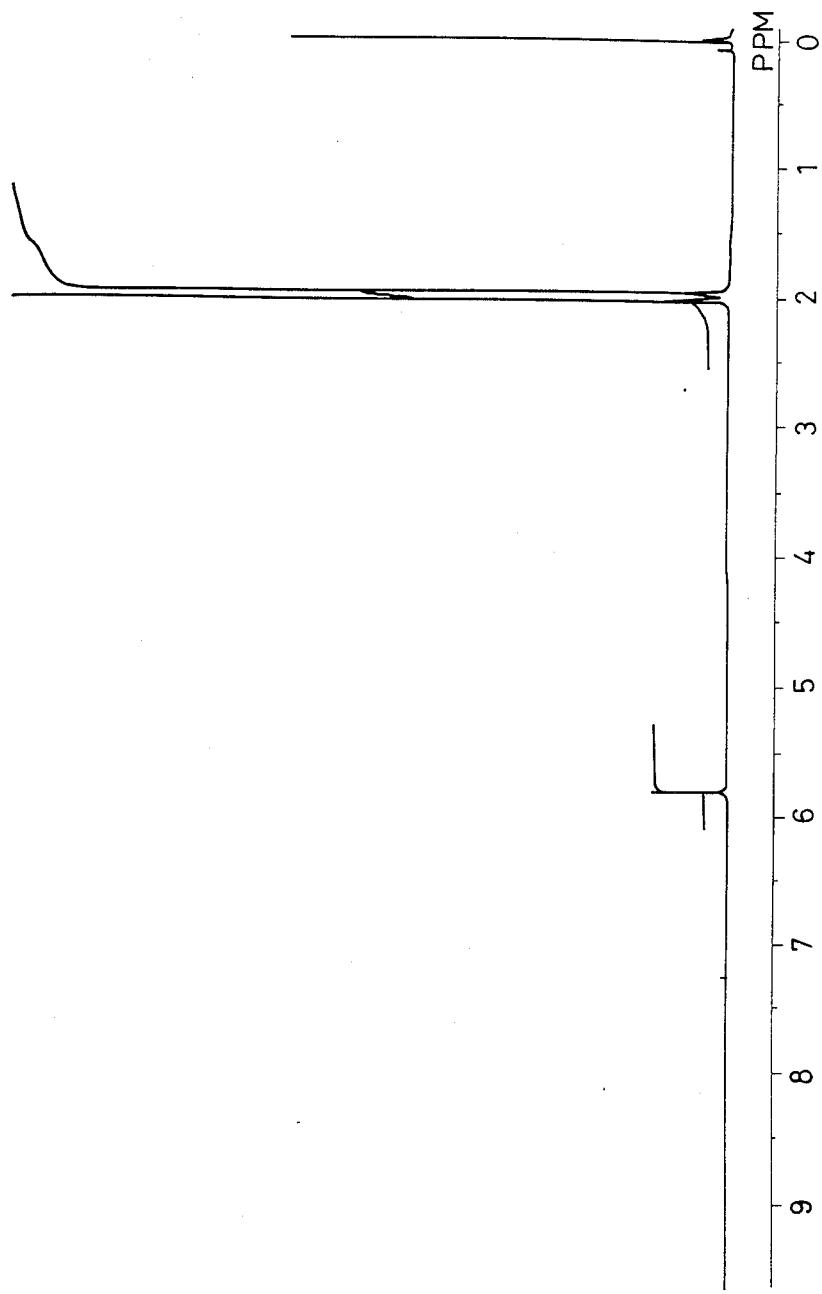
Figure 11:
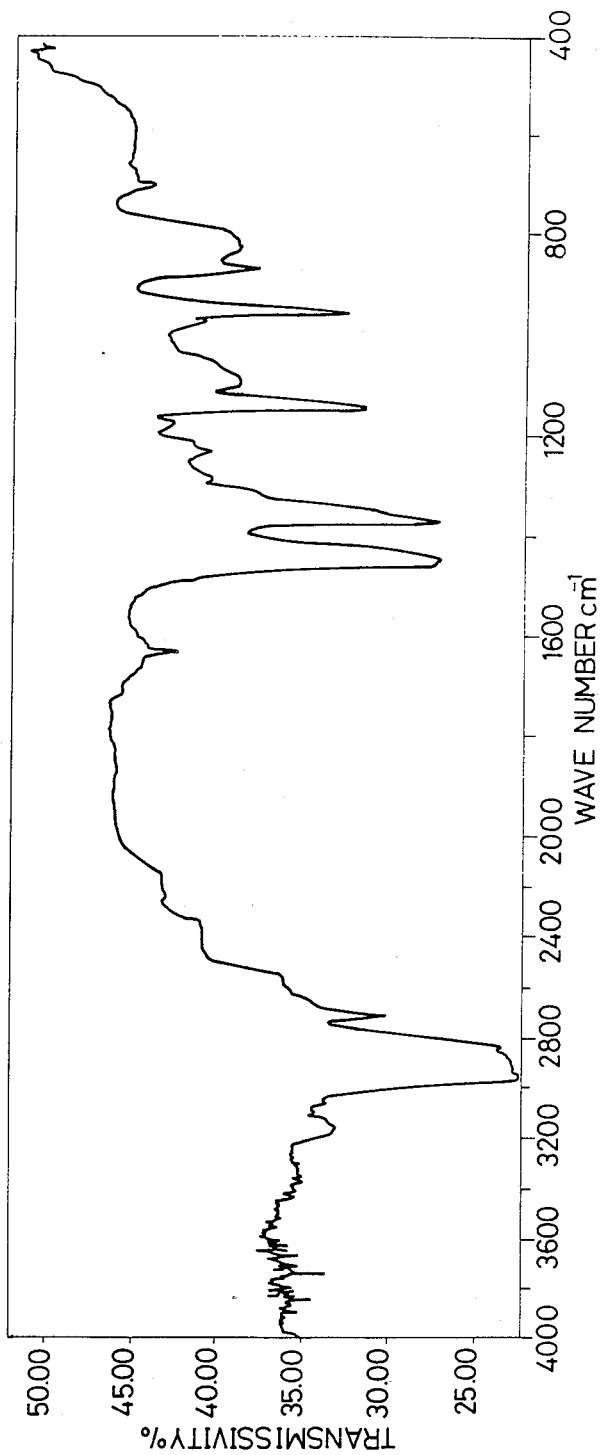
FIGS. 11 through 16 show IR spectra of atactic polypropylenes obtained by polymerization of propylene using catalysts of this invention and conventional catalysts.
Figure 12:
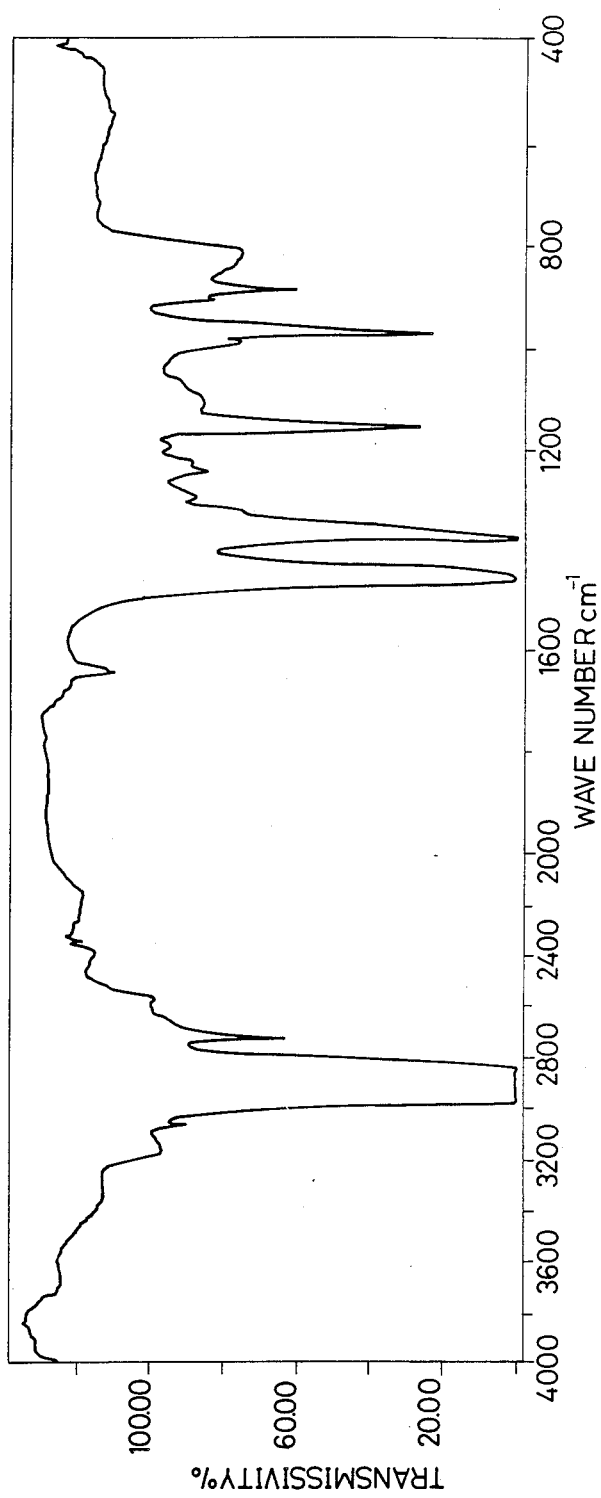
Figure 13:
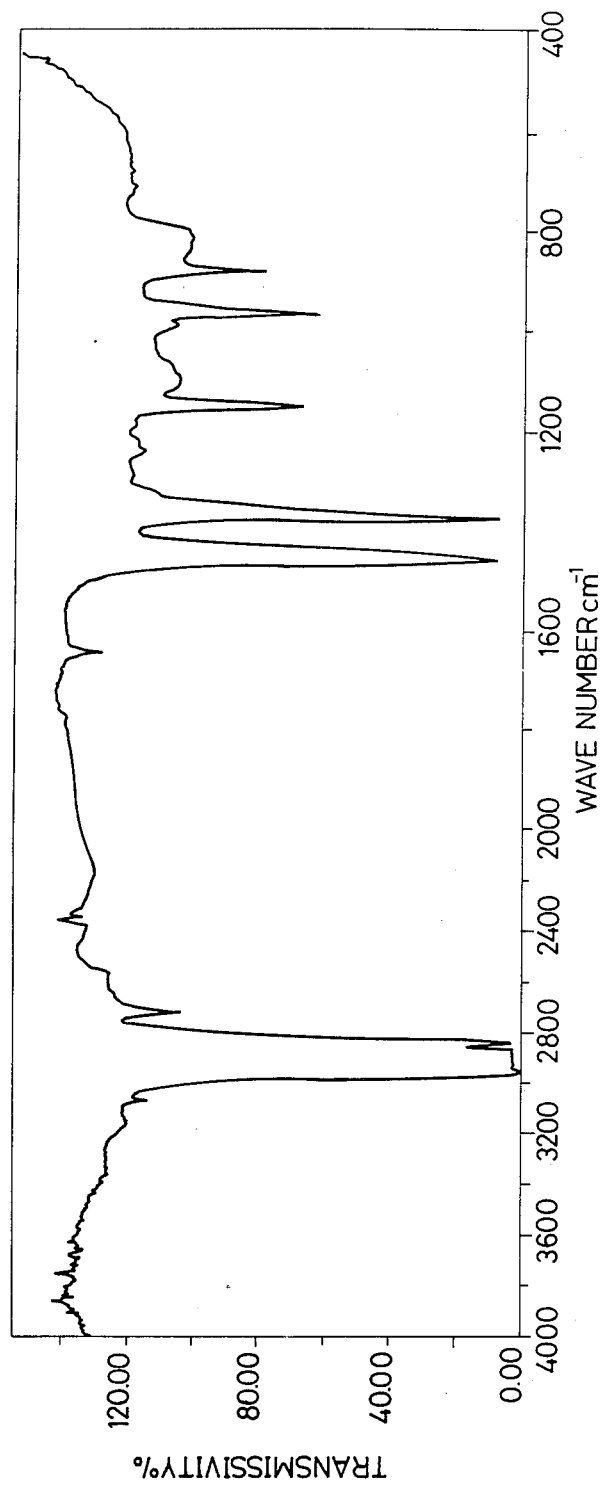
Figure 14:
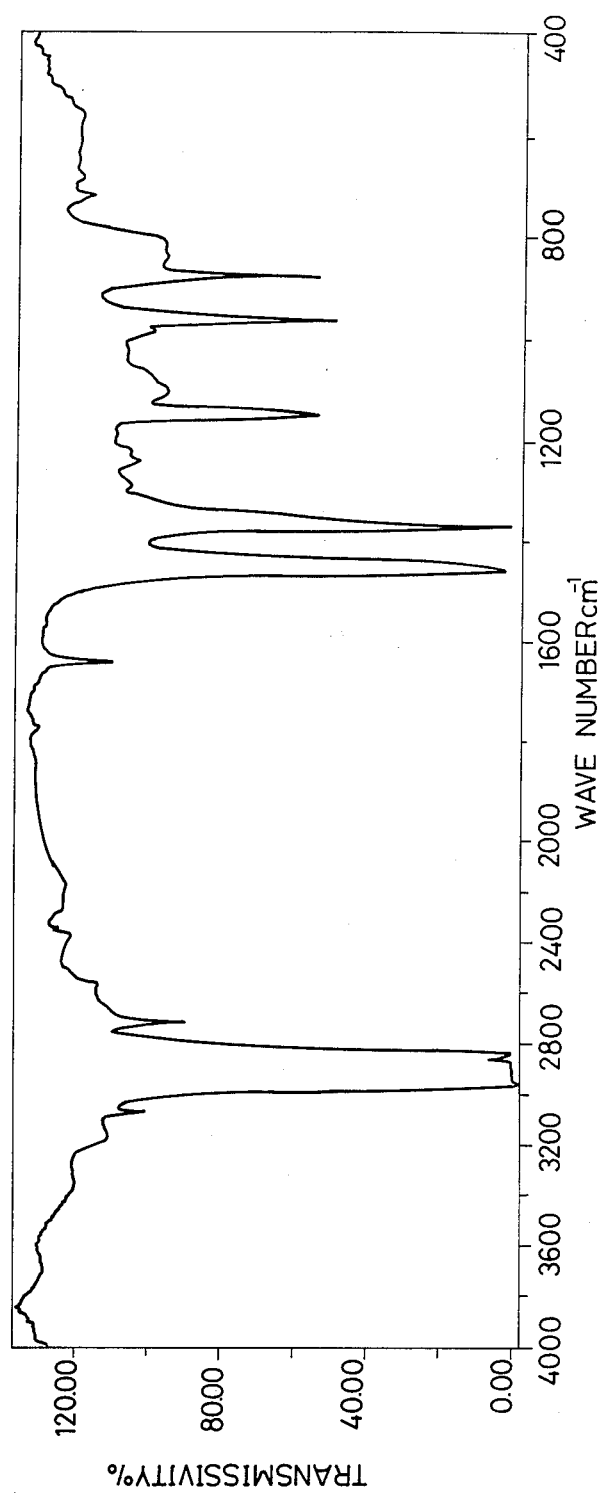
Figure 15:
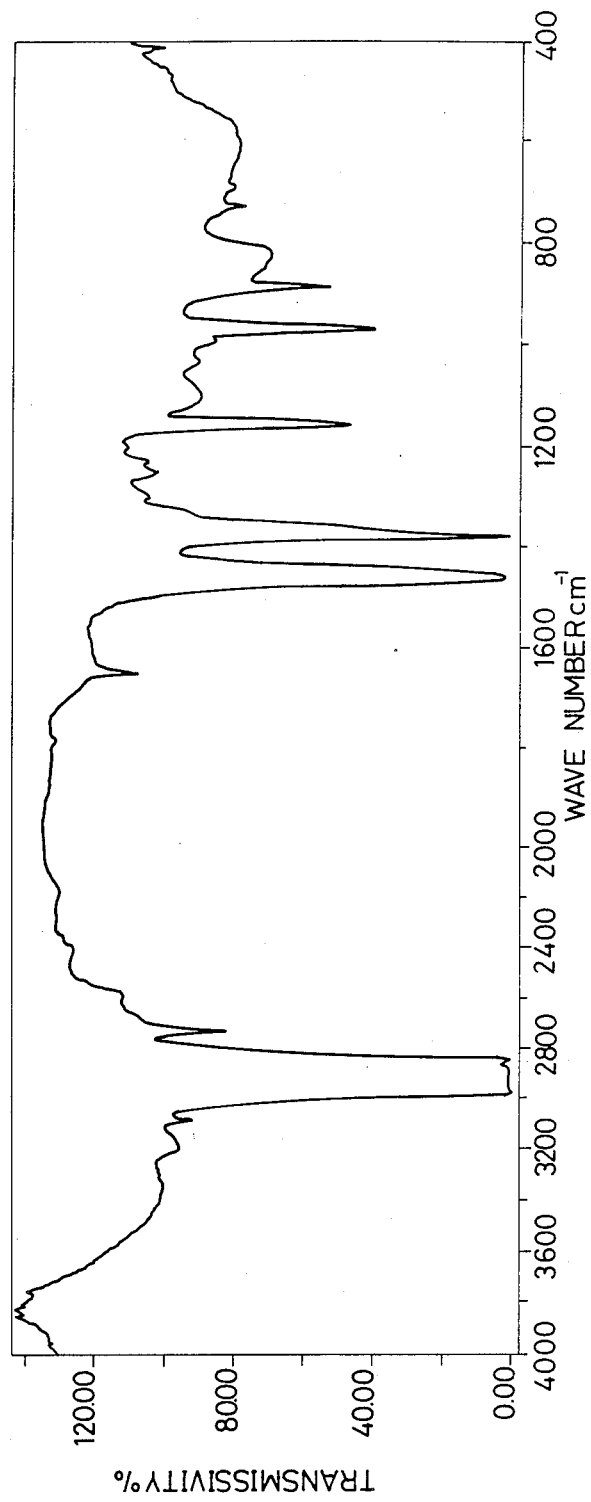
Figure 16:
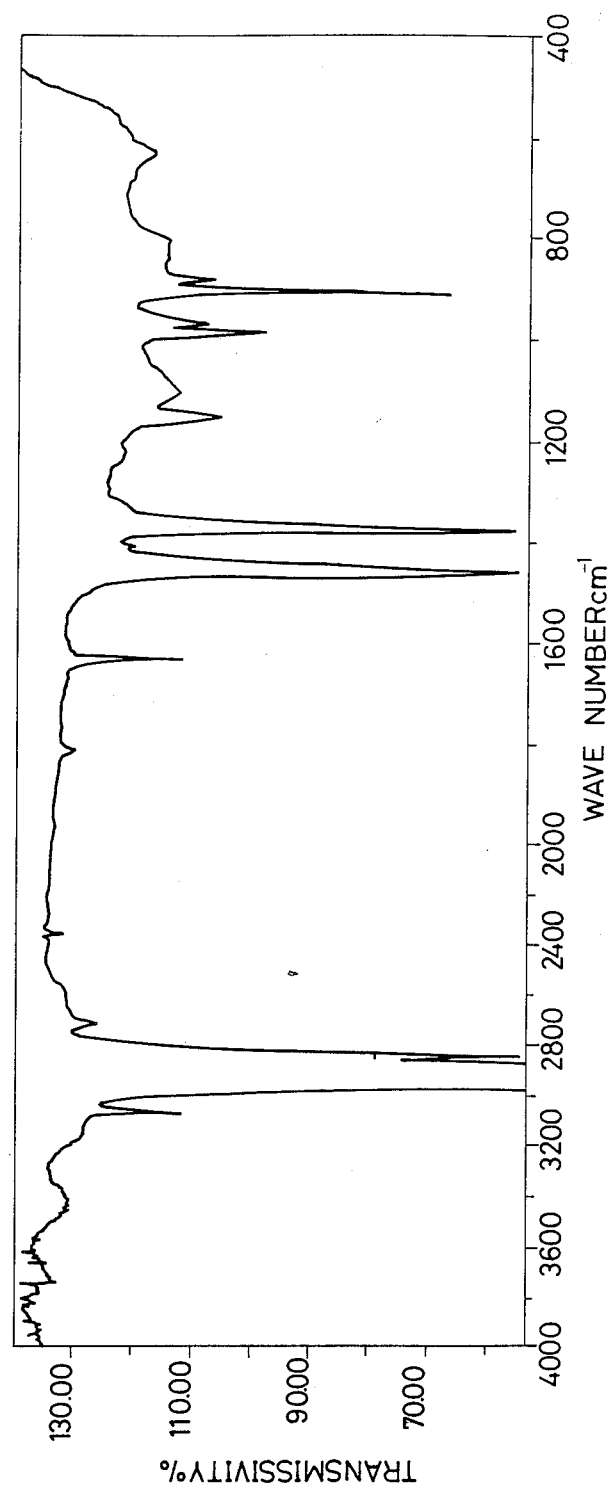

NMR spectrum: As shown in FIG. 10

EXAMPLE 6

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2,4-trimethylcyclopentadienyl)zirconium dichloride prepared in Example 4 in that order, and the mixture was heated to 50° C.

Propylene was then introduced continuously to the autoclave so that the internal pressure was maintained at 8 Kg/cm$^2$G, and polymerization was continued under this condition for 1.5 hours. At the end of reaction, methanol was added to decompose the catalyst and atactic polypropylene formed was collected and dried (yield: 260 g). Its IR spectrum showed peaks at 1651 cm$^{-1}$ and 887 cm$^{-1}$, indicating vinylidene-type terminal structure.

EXAMPLE 7

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2,3,4-tetramethylcyclopentadienyl)zirconium dichloride prepared in Example 5 in that order, and the mixture was heated to 50° C.

Propylene was then introduced continuously to the autoclave so that the internal pressure was maintained at 8 Kg/cm$^2$G, and polymerization was continued under this condition for two hours. At the end of reaction, methanol was added to decompose the catalyst and atactic polypropylene formed was collected and dried (yield: 260 g). Its IR spectrum showed peaks at 1782 cm$^{-1}$, 1651 cm$^{-1}$ and 887 cm$^{-1}$, indicating vinylidene-type terminal structure.

EXAMPLE 8

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,3-dimethylcyclopentadienyl)zirconium dichloride prepared in Example 2 in that order, and the mixture was heated to 50° C.

Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 450 g). Its IR spectrum showed peaks at 1651 cm$^{-1}$ and 887 cm$^{-1}$, indicating vinylidene-type terminal structure.

COMPARATIVE EXAMPLE 1

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(pentamethylcyclopentadienyl)zirconium dichloride in that order, and the mixture was heated to 50° C.

Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 210 g). Its IR spectrum showed the presence of peaks at 1639 cm$^{-1}$, 991 cm$^{-1}$ and 910 cm$^{-1}$, indicating vinyl-type terminal structure.

EXAMPLE 9

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2-dimethylcyclopentadienyl)zirconium dichloride prepared in Example 1 in that order, and the mixture was heated to 50° C.

Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 300 g). Its IR spectrum showed peaks at 1651 cm$^{-1}$ and 887 cm$^{-1}$, indicating vinylidene-type terminal structure.

EXAMPLE 10

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2,3-trimethylcyclopentadienyl)zirconium dichloride prepared in Example 3 in that order, and the mixture was heated to 50° C.

Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 180 g). Its IR spectrum showed peaks at 1651 cm$^{-1}$ and 887 cm$^{-1}$, indicating vinylidene-type terminal structure.

IR absorption spectra of the atactic polypropylenes obtained in Examples 6, 7, 8, 9 and 10 and in Comparative Example 1 are shown in FIGS. 11, 12, 13, 14, 15 and 16, respectively; $^{13}$C—NMR data for the polymers of Examples 6, 7 and 10 are shown in Table 1; and GPC data for the polymers of Examples 6, 7, 8, 9 and 10 and of Comparative Example 1 are shown in Table 2.

TABLE 1

($^{13}$C-NMR data)

| Transition metal compound | Example No. | | |
|---|---|---|---|
| | 6 $(1,2,4\text{-Me}_3\text{C}_5\text{H}_2)_2\text{ZrCl}_2$ | 7 $(1,2,3,4\text{-Me}_4\text{-C}_5\text{H})_2\text{ZrCl}_2$ | 10 $(1,2,3\text{-Me}_3\text{-C}_5\text{H}_2)_2\text{ZrCl}_2$ |
| mmmm | 0.076 | 0.076 | 0.040 |
| mmmr | 0.141 | 0.136 | 0.096 |
| rmmr | 0.081 | 0.077 | 0.068 |
| mmrr | 0.118 | 0.117 | 0.095 |
| mmrm + rrmr | 0.254 | 0.254 | 0.234 |
| mrmr | 0.137 | 0.137 | 0.162 |
| rrrr | 0.047 | 0.049 | 0.072 |
| mrrr | 0.093 | 0.096 | 0.136 |
| mrrm | 0.055 | 0.050 | 0.097 |
| mm | 0.297 | 0.289 | 0.204 |
| mr | 0.508 | 0.508 | 0.491 |
| rr | 0.195 | 0.203 | 0.305 |

TABLE 2

(GPC data)

| Example No. | Transition metal compound | $\overline{M}_n$ | $\overline{M}_w$ | $\overline{M}_z$ | $\overline{M}_w/\overline{M}_n$ |
|---|---|---|---|---|---|
| 6 | $(1,2,4\text{-Me}_3\text{-C}_5\text{H}_2)_2\text{ZrCl}_2$ | 4,800 | 13,000 | 22,000 | 2.7 |
| 7 | $(1,2,3,4\text{-Me}_4\text{-C}_5\text{H})_2\text{ZrCl}_2$ | 1,900 | 6,400 | 13,000 | 3.4 |
| 8 | $(1,3\text{-Me}_2\text{-C}_5\text{H}_3)_2\text{ZrCl}_2$ | 1,800 | 4,900 | 9,000 | 2.7 |
| 9 | $(1,2\text{-Me}_2\text{-C}_5\text{H}_3)_2\text{ZrCl}_2$ | 980 | 3,000 | 6,000 | 3.1 |
| 10 | $(1,2,3\text{-Me}_3\text{-C}_5\text{H}_2)_2\text{ZrCl}_2$ | 2,200 | 5,600 | 10,000 | 2.5 |
| Comp. Ex. 1 | $(1,2,3,4,5\text{-Me}_5\text{-C}_5)_2\text{ZrCl}_2$ | 140 | 300 | 530 | 2.1 |

EXAMPLE 11

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2,4-trimethylcyclopentadienyl)zirconium dichloride prepared in Example 4 in that order, and the mixture was heated to 50° C. Propylene was then introduced continuously to the autoclave so that the internal pressure was maintained at 8 Kg/cm$^2$G, and polymerization was continued under this condition for 1.5 hours. At the end of reaction, methanol was added to decompose the catalyst and atactic polypropylene formed was collected and dried (yield: 260 g). The catalyst activity was 95 Kg/gZr.hr and the molecular weight of the polymer obtained was 13,000.

EXAMPLE 12

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2,3,4-tetramethylcyclopentadienyl)zirconium dichloride prepared in Example 5 in that order, and the mixture was heated to 50° C. Propylene was then introduced continuously to the autoclave so that the internal pressure was maintained at 8 Kg/cm$^2$G, and polymerization was continued under this condition for two hours. At the end of reaction, methanol was added to decompose the catalyst and atactic polypropylene formed was collected and dried (yield: 260 g). The catalyst activity was 71 Kg/gZr.hr and the molecular weight of the polymer obtained was 6,500.

EXAMPLE 13

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,3-dimethylcyclopentadienyl)zirconium dichloride prepared in Example 2 in that order, and the mixture was heated to 50° C. Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 450 g). The catalyst activity was 61 Kg/gZr.hr and the molecular weight of the polymer obtained was 5,000.

COMPARATIVE EXAMPLE 2

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(cyclopentadienyl)zirconium dichloride in that order, and the mixture was heated to 50° C. Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 150 g). The catalyst activity was 20 Kg/gZr.hr and the molecular weight of the polymer obtained was 1,300.

COMPARATIVE EXAMPLE 3

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(pentamethylcyclopentadienyl)zirconium dichloride in that order, and the mixture was heated to 50° C. Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 210 g). The catalyst activity was 28 Kg/gZr.hr and the molecular weight of the polymer obtained was 300.

COMPARATIVE EXAMPLE 4

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(methylcyclopentadienyl)zirconium dichloride in that order, and the mixture was heated to 50° C. Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 220 g). The catalyst activity was 30 Kg/gZr.hr and the molecular weight of the polymer obtained was 800.

COMPARATIVE EXAMPLE 5

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(t-butylcyclopentadienyl)zirconium dichloride in that order, and the mixture was heated to 50° C. Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 160 g). The catalyst activity was 22 Kg/gZr.hr and the molecular weight of the polymer obtained was 500.

EXAMPLE 14

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2-dimethylcyclopentadienyl)zirconium dichloride prepared in Example 1 in that order, and the mixture was heated to 50° C. Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 300 g). The catalyst activity was 41 Kg/gZr.hr and the molecular weight of the polymer obtained was 3,000.

EXAMPLE 15

[Polymerization]

A stainless steel autoclave (capacity: 1.5 liters), with its internal air thoroughly displaced by nitrogen gas, was charged with 450 ml of pure toluene, 6.3 millimoles of methylaluminoxane (M.W.: 909; product of Toyo Stauffer Chemical Co.) and 0.02 millimole of bis(1,2,3-trimethylcyclopentadienyl)zirconium dichloride prepared in Example 3 in that order, and the mixture was heated to 50° C. Propylene was then introduced continuously to the autoclave so that the internal pressure was maintained at 8 Kg/cm$^2$G, and polymerization was continued under this condition for four hours. At the end of reaction, methanol was added to decompose the catalyst and atactic polypropylene formed was collected and dried (yield: 180 g). The catalyst activity was 25 Kg/gZr.hr and the molecular weight of the polymer obtained was 5,600.

EXAMPLE 16

[Polymerization]

A stainless steel autoclave (capacity: 1.5 liters), with its internal air thoroughly displaced by nitrogen gas, was charged with 450 ml of pure toluene, 1.5 millimoles of methylaluminoxane (M.W.: 909; product of Toyo Stauffer Chemical Co.) and 0.002 millimole of bis(1,2,3-trimethylcyclopentadienyl)zirconium dichloride prepared in Example 3 in that order, and the mixture was heated to 50° C. Ethylene was then introduced continuously to the autoclave so that the internal pressure was maintained at 4 Kg/cm$^2$G, and polymerization was continued under this condition for two hours. At the end of reaction, methanol was added to decompose the catalyst and atactic polyethylene formed was collected and dried (yield: 30 g). The catalyst activity was 82 Kg/gZr.hr and the molecular weight of the polymer obtained was 177,000.

COMPARATIVE EXAMPLE 6

[Polymerization]

A stainless steel autoclave (capacity: 1.5 liters), with its internal air thoroughly displaced by nitrogen gas, was charged with 450 ml of pure toluene, 2.0 millimoles of methylaluminoxane (M.W.: 909; product of Toyo Stauffer Chemical Co.) and 0.003 millimole of bis(pentamethylcyclopentadienyl)zirconium dichloride in that order, and the mixture was heated to 50° C. Ethylene was then introduced continuously to the autoclave so that the internal pressure was maintained at 4 Kg/cm$^2$G, and polymerization was continued under this condition for two hours. At the end of reaction, methanol was added to decompose the catalyst and polyethylene formed was collected and dried (yield: 18 g). The catalyst activity was 32 Kg/gZr.hr and the molecular weight of the polymer obtained was 70,000.

What is claimed is:

1. Bis(di-substituted-cyclopentadienyl)zirconium dihalides represented by the following general formula [I] or [II],

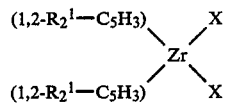

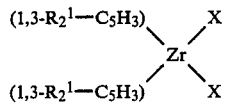

wherein $R^1$ denotes a substituent group on the cyclopentadienyl ring which is an alkyl radical of 1 to 5 carbon atoms; $R_2^1$—$C_5H_3$ stands for a di-substituted cyclopentadienyl radical; and X is a halogen atom.

2. Bis(tri-substituted-cyclopentadienyl)zirconium dihalides represented by the following general formula or,

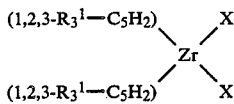

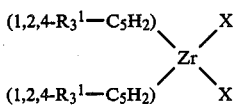

wherein $R^1$ denotes a substituent group on the cyclopentadienyl ring which is an alkyl radical of 1 to 5 carbon atoms; $R_3^1$—$C_5H_2$ stands for a tri-substituted cyclopentadienyl radical; and X is a halogen atom.

3. Bis(tetra-substituted-cyclopentadienyl)zirconium dihalides represented by the following general formula,

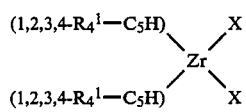

wherein $R^1$ denotes a substituent group on the cyclopentadienyl ring which is an alkyl radical of 1 to 5 carbon atoms; $R_4^1$—$C_5H$ stands for a tetra-substituted cyclopentadienyl radical; and X is a halogen atom.

* * * * *